US 11,717,589 B2

(12) United States Patent
Zhang et al.

(10) Patent No.: US 11,717,589 B2
(45) Date of Patent: Aug. 8, 2023

(54) TRAY DISINFECTION DEVICE

(71) Applicants: Nuctech Company Limited, Beijing (CN); Tsinghua University, Beijing (CN)

(72) Inventors: Li Zhang, Beijing (CN); Zhiqiang Chen, Beijing (CN); Qingping Huang, Beijing (CN); Mingzhi Hong, Beijing (CN); Yue Li, Beijing (CN); Bo Li, Beijing (CN); Minghua Qiu, Beijing (CN); Yanhua Lu, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 72 days.

(21) Appl. No.: 17/136,781

(22) Filed: Dec. 29, 2020

(65) Prior Publication Data
US 2021/0330848 A1    Oct. 28, 2021

(30) Foreign Application Priority Data

Apr. 26, 2020 (CN) .......................... 202010341340.6

(51) Int. Cl.
*A61L 2/26* (2006.01)
*A61L 2/10* (2006.01)

(52) U.S. Cl.
CPC .................. *A61L 2/26* (2013.01); *A61L 2/10* (2013.01); *A61L 2202/11* (2013.01); *A61L 2202/122* (2013.01)

(58) Field of Classification Search
CPC ..... A61L 2/10; A61L 2/24; A61L 2/26; A61L 2202/11; A61L 2202/122
See application file for complete search history.

(56) References Cited

U.S. PATENT DOCUMENTS

| 5,958,336 A | * | 9/1999 | Duarte | ...................... A61L 2/10 250/455.11 |
| 2007/0012340 A1 | * | 1/2007 | Jones | ........................ A61L 2/10 134/131 |

FOREIGN PATENT DOCUMENTS

| CN | 1031027 A | | 2/1989 | |
| CN | 200970362 Y | | 11/2007 | |
| CN | 101352575 A | | 1/2009 | |
| CN | 201631726 U | * | 11/2010 | ............... A61L 2/10 |
| CN | 202814003 U | | 3/2013 | |
| CN | 204631271 U | | 9/2015 | |
| CN | 204631271 U | * | 9/2015 | |

(Continued)

OTHER PUBLICATIONS

"Caligari Becomes the First European Airport to Install a New UV-C Surface Disinfection System", Italy, Mar. 25, 2020, URL: airportinternational.com/2020/03/25/caligari-becomes-the-first-european-airport-to-install-a-new-uv-c-surface-disinfection-system (Year: 2020).*

(Continued)

*Primary Examiner* — David E Smith
(74) *Attorney, Agent, or Firm* — Knobbe, Martens, Olson & Bear LLP

(57) ABSTRACT

A tray disinfection devices for a security inspection system can include a frame, a disinfection channel on the frame, and a conveyor on the frame. An ultraviolet disinfection lamp is arranged in the disinfection channel. The conveyor on the frame is configured to convey a tray to pass through the disinfection channel so as to disinfect the tray through an irradiation of the ultraviolet disinfection lamp.

7 Claims, 3 Drawing Sheets

(56) References Cited

FOREIGN PATENT DOCUMENTS

| CN | 204637044 U | | 9/2015 |
|----|-------------|---|--------|
| CN | 105435289 A | | 3/2016 |
| CN | 206352466 U | | 7/2017 |
| CN | 207928512 U | | 10/2018 |
| CN | 208186953 U | | 12/2018 |
| CN | 109174766 A | | 1/2019 |
| CN | 209236953 U | | 8/2019 |
| CN | 209450989 U | | 10/2019 |
| CN | 209900158 U | * | 1/2020 |
| CN | 210019654 U | | 2/2020 |
| CN | 210320774 U | * | 4/2020 |
| CN | 210320774 U | | 4/2020 |
| CN | 211903654 U | | 11/2020 |
| DE | 102009055731 A1 | | 5/2010 |
| JP | S40-36291 Y1 | | 11/1963 |
| JP | S52-62997 U | | 11/1975 |
| JP | H06-261720 A | | 9/1994 |
| JP | H08-42829 A | | 2/1996 |
| JP | H11-56982 A | | 3/1999 |
| JP | 2005-312978 A | | 11/2005 |
| JP | 2005319172 A | | 11/2005 |

OTHER PUBLICATIONS

Extended European Search Report for Application No. 20216255.8 dated Jun. 4, 2021 in 7 pages.

Office Action with English Translation Issued for Japanese Patent Application No. 2020-205018 dated Feb. 1, 2022 in 8 pages.

News/Cagliari becomes the first European airport to install a new UV-C surface desinfection system.[online], Italy, Mar. 25, 2020, [Searched on Jan. 24, 2021], Internet<URL:airportinternational.com/2020/03/25/cagliari-becomes-the-first-european-airport-to-install-a-new-uv-c-surface-desinfection-system.>.

Office Action Issued for Australian Patent Application No. 2020289784 dated Dec. 1, 2021 in 8 pages.

Office Action with English Translation Issued for Chinese Patent Application No. 202010341340.6 dated Dec. 21, 2021 in 13 pages.

European Communication pursuant to Article 94(3) EPC dated Sep. 27, 2022 in European Application No. 20 216 255.8, 4 pages.

Japan Patent Office Notice of Reasons for Refusal dated Aug. 25, 2022 in Japanese Application No. 2020-205018, 10 pages.

Japan Patent Office Notice of Reasons for Refusal dated Jan. 10, 2023 in Japanese Application No. 2020-205018, with English translation, 6 pages.

* cited by examiner

TRAY DISINFECTION DEVICE

CROSS-REFERENCE TO RELATED APPLICATION

This application claims priority to Chinese Patent Application No. 202010341340.6, filed on Apr. 26, 2020, the disclosure of which is hereby incorporated herein by reference in its entirety.

TECHNICAL FIELD

The disclosed technology generally relates to the field of security inspection apparatus, and particularly to a tray disinfection device.

BACKGROUND

At present, public places such as customs ports, airports, subway stations, railway stations, postal logistics and large-scale event venues are generally equipped with luggage security inspection apparatuses. When in use, a luggage item is placed in a tray and then passes through the luggage security inspection apparatus for security inspection. The tray, as a reusable tool, will be repeatedly touched by passengers. However, there is currently no disinfection device specifically for trays. Daily disinfection of trays is usually performed by manually spraying disinfectant and wiping. However, it is impossible to perform manual disinfection every time the tray is used, so there is a blind spot for disinfection which is prone to cross infection, and the work efficiency is low.

SUMMARY

Some embodiments of the disclosed technology provide a tray disinfection device for a security inspection system, including a frame; a disinfection channel on the frame, wherein an ultraviolet disinfection lamp is arranged in the disinfection channel; and a conveyor on the frame is configured to convey a tray to pass through the disinfection channel, so as to disinfect the tray through an irradiation of the ultraviolet disinfection lamp.

In some embodiments according to the disclosed technology, at least part of an inner side wall of the disinfection channel is provided with a reflective layer.

In some embodiments according to the disclosed technology, a temperature control device is further arranged in the disinfection channel to control a temperature in the disinfection channel.

In some embodiments according to the disclosed technology, the disinfection channel includes: a base plate connected to the frame and located above the conveyor, wherein the ultraviolet disinfection lamp is installed on the base plate; a first bottom shading plate below the conveyor; and two first side shading plates on both sides of the conveyor respectively, wherein the two first side shading plates, the first bottom shading plate and the base plate enclose to form the disinfection channel.

In some embodiments according to the disclosed technology, the disinfection channel further includes a first connector adapted to connect the base plate to the frame.

In some embodiments according to the disclosed technology, the first connector is made of a plate-shaped member.

In some embodiments according to the disclosed technology, at least one end of the conveyor along a conveying direction is provided with a shading channel in communication with the disinfection channel.

In some embodiments according to the disclosed technology, the shading channel includes: a top shading plate connected to the frame and located above the conveyor; a second bottom shading plate below the conveyor; and two second side shading plates on both sides of the conveyor respectively, wherein the two second side shading plates, the second bottom shading plate and the top shading plate enclose to form the shading channel.

In some embodiments according to the disclosed technology, the shading channel further includes a second connector adapted to connect the top shading plate to the frame.

In some embodiments according to the disclosed technology, the second connector is made of a plate-shaped member.

BRIEF DESCRIPTION OF THE DRAWINGS

The features and advantages of the disclosed technology will be understood more clearly with reference to the drawings. The drawings are merely schematic and should not be construed as limiting the disclosed technology. In the drawings.

DETAILED DESCRIPTION

Although the disclosed technology will be fully described with reference to the drawings containing example embodiments of the disclosed technology, it should be understood that those skilled in the art may modify the technology described herein while obtaining the technical effects of the disclosed technology. Therefore, it should be understood that the above description is a broad disclosure for those ordinary skilled in the art, and its content is not intended to limit the exemplary embodiments described in the disclosed technology.

In addition, in the following detailed description, for the convenience of explanation, many specific details are set forth to provide a comprehensive understanding of the embodiments of the disclosed technology. As may be appreciated, one or more embodiments can be implemented without these specific details. In other cases, well-known structures and devices are shown in diagrammatic form to simplify the drawings.

According to a general inventive concept of the disclosed technology, there is provided a tray disinfection device for a security inspection system, including: a frame; a disinfection channel arranged on the frame, wherein an ultraviolet disinfection lamp is arranged in the disinfection channel;

and a conveyor arranged on the frame and configured to convey a tray to pass through the disinfection channel, so as to disinfect the tray through an irradiation of the ultraviolet disinfection lamp.

Figure 1:
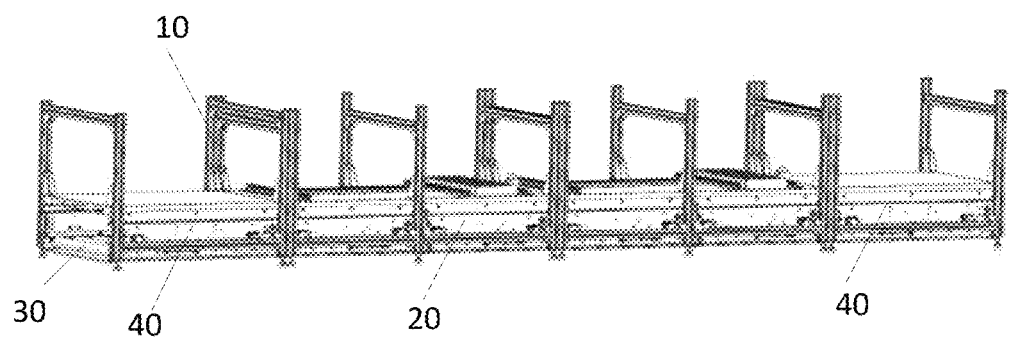
FIG. 1 shows a schematic structural diagram of a tray disinfection device for a security inspection system according to an exemplary embodiment of the disclosed technology.
Figure 2:
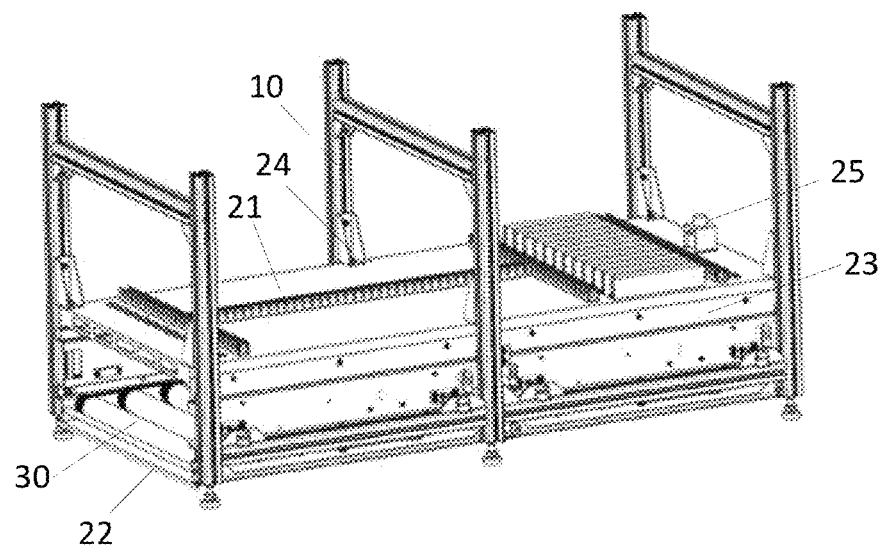
FIG. 2 shows a perspective view of a disinfection channel according to an exemplary embodiment of the disclosed technology.
Figure 3:
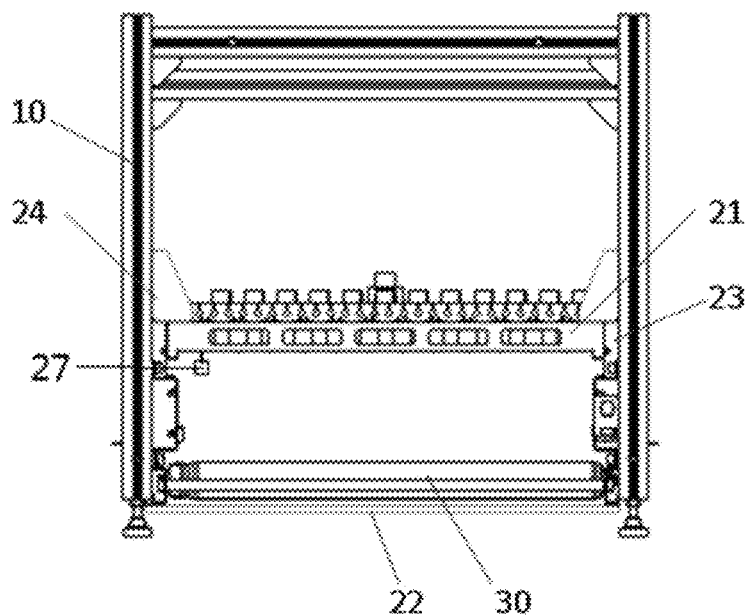
FIG. 3 shows a cross-sectional view of the disinfection channel shown in FIG. 2.
Figure 4:
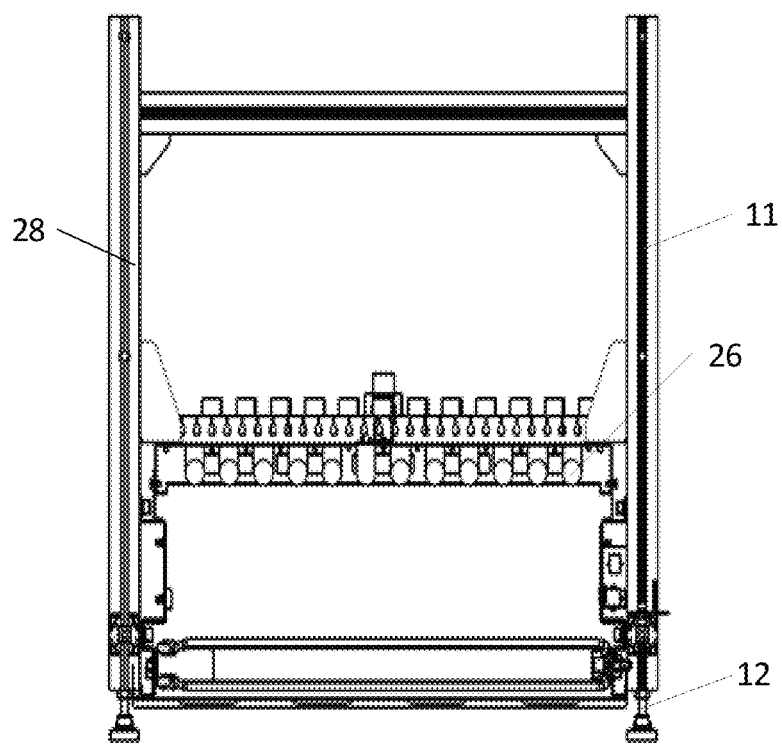
FIG. 4 shows another cross-sectional view of the disinfection channel shown in FIG. 2.
Figure 5:
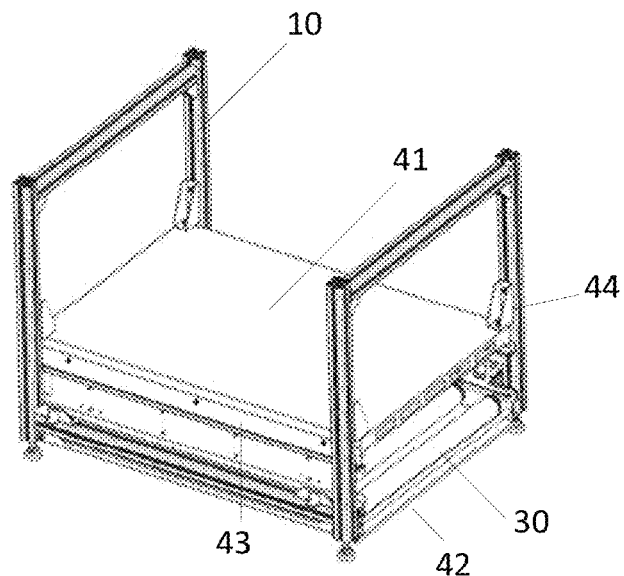
FIG. 5 shows a schematic structural diagram of a shading channel according to an exemplary embodiment of the disclosed technology.
Figure 6:
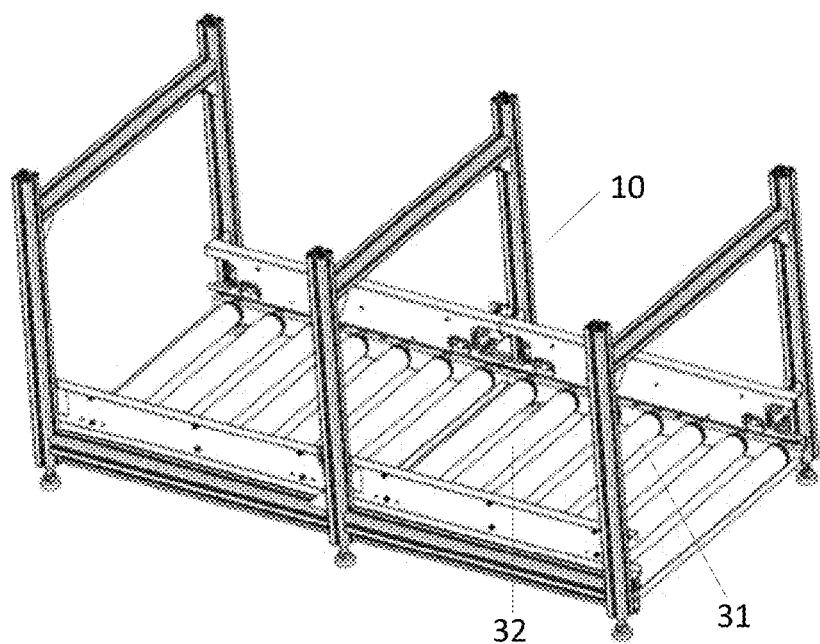
FIG. 6 shows a schematic structural diagram of a conveyor according to an exemplary embodiment of the disclosed technology.

FIG. 1 shows a schematic structural diagram of the tray disinfection device for the security inspection system according to an exemplary embodiment of the disclosed technology; FIG. 2 shows a perspective view of the disinfection channel according to an exemplary embodiment of the disclosed technology; FIG. 3 shows a cross-sectional view of the disinfection channel shown in FIG. 2; FIG. 4 shows another cross-sectional view of the disinfection channel shown in FIG. 2; FIG. 5 shows a schematic structural diagram of a shading channel according to an exemplary embodiment of the disclosed technology; and FIG. 6 shows a schematic structural diagram of the conveyor according to an exemplary embodiment of the disclosed technology.

In an exemplary embodiment of the disclosed technology, as shown in FIG. 1, the tray disinfection device for the security inspection system includes a frame 10 and a disinfection channel 20 arranged on the frame 10. The disinfection channel 20 is elongated and provided with an ultraviolet disinfection lamp 26 which can provide an effective dose of ultraviolet rays. The tray disinfection device also includes a conveyor 30 which is arranged on the frame 10 and is configured to convey the tray to pass through the disinfection channel 20, so as to disinfect the tray during continuous operation through an irradiation of the ultraviolet disinfection lamp 26.

The tray disinfection device for the security inspection system provided by the disclosed technology rapidly kills bacteria and viruses on the surface of the tray by irradiating the tray during operation with the ultraviolet disinfection lamp 26 arranged in the disinfection channel 20 for a short time. Compared with the traditional disinfection and sterilization methods, the tray disinfection device has the characteristics of fast sterilization speed, simple operation, environmental protection and no secondary pollution.

In an exemplary embodiment of the disclosed technology, the ultraviolet disinfection lamp 26 may radiate ultraviolet rays, for example, with a wavelength of 253.7 nm, which has the strongest bactericidal ability and which can quickly kill bacteria and viruses such as bacterial propagules, spores, mycobacteria, coronaviruses, fungi, rickettsiae and chlamydiae.

In an exemplary embodiment of the disclosed technology, as shown in FIGS. 3 and 4, an inner side wall of the disinfection channel 20 is provided with a reflective layer 28, so that the ultraviolet rays emitted by the ultraviolet disinfection lamp 26 may be irradiated to each surface of the tray after being reflected, so as to realize a comprehensive disinfection of the tray. However, those skilled in the art should understand that in some other embodiments of the disclosed technology, the reflective layer 28 may be provided only on a part of the inner side wall of the disinfection channel 20.

In an exemplary embodiment of the disclosed technology, as shown in FIG. 2, the tray disinfection device further includes a controller 25 configured to control an operating state of the ultraviolet disinfection lamp 26 in the disinfection channel 20.

In an exemplary embodiment of the disclosed technology, as shown in FIGS. 3 and 4, a temperature control device 27 is further provided in the disinfection channel 20 to control the temperature in the disinfection channel 20. The temperature control device may include, for example, a temperature sensor and a fan. The temperature sensor is configured to sense the temperature in the disinfection channel 20 and adjust a fan speed based on the sensed temperature in the disinfection channel, so as to realize real-time control of the temperature in the disinfection channel 20. In this way, the temperature in the disinfection channel 20 may be kept stable. For example, the temperature in the disinfection channel may be controlled at 45° C.±5° C. to avoid the effect on ultraviolet rays when the temperature is too high or too low, thereby ensuring the disinfection effect of the tray disinfection device.

In this embodiment, the temperature control device 27 may also be connected to the controller 25, so as to control the operating state of the temperature control device 27 through the controller 25.

In an exemplary embodiment of the disclosed technology, as shown in FIGS. 1 to 4, the disinfection channel 20 includes a base plate 21, a first bottom shading plate 22, and two first side shading plates 23. The base plate 21 is connected to the frame 10 and is located above the conveyor 30. The ultraviolet disinfection lamp 26 is installed on the base plate 21. The first bottom shading plate 22 is arranged below the conveyor 30. The two first side shading plates 23 are respectively arranged on both sides of the conveyor 30. The two first side shading plates 23, the first bottom shading plate 22 and the base plate 21 enclose to form the disinfection channel 20. In this embodiment, the first bottom shading plate 22 and the first side shading plate 23 may be made of, for example, mirror stainless steel. In this way, there is no need to additionally provide a reflective layer on the inner side wall of the disinfection channel, and the ultraviolet rays emitted by the ultraviolet disinfection lamp 26 is reflected directly by the mirror stainless steel.

In an exemplary embodiment of the disclosed technology, as shown in FIGS. 1 to 4, the disinfection channel 20 further includes a first connector 24 adapted to connect the base plate 21 to the frame 10. The first connector 24 includes a first connecting part adapted for connection (for example, bolted connection) with the base plate 21 and a second connecting part adapted for connection (for example, bolted connection) with the frame 10. The first connector 24 further includes a reinforcing part adapted for connection with the first connecting part and the second connecting part to enhance the robustness of the first connector 24.

In an exemplary embodiment of the disclosed technology, as shown in FIGS. 1 to 4, the first connector 24 is made of a plate-shaped member by stamping.

In an exemplary embodiment of the disclosed technology, as shown in FIGS. 1 and 5, both ends of the conveyor 30 along the conveying direction are provided with shading channels 40 in communication with the disinfection channel 20 so as to prevent the ultraviolet rays from leaking and causing harm. However, those skilled in the art should understand that in some other embodiments of the disclosed technology, the shading channel 40 may be provided only at one end of the conveyor 30 along the conveying direction.

In an exemplary embodiment of the disclosed technology, as shown in FIGS. 1 and 5, the shading channel 40 includes a top shading plate 41, a second bottom shading plate 42 and two second side shading plates 43. The top shading plate 41 is connected to the frame 10 and is located above the conveyor 30. The second bottom shading plate 42 is arranged below the conveyor 30. The two second side shading plates 43 are respectively arranged on both sides of the conveyor 30. The two second side shading plates 43, the second bottom shading plate 42 and the top shading plate 41 enclose to form the shading channel 40. In this embodiment, the top shading plate 41, the second bottom shading plate 42 and the second side shading plates 43 may be made of, for example, stainless steel. Preferably, inner surfaces of the top shading plate 41, the second bottom shading plate 42 and the second side shading plates 43 are subjected to surface treatments, such as blackening, frosting, hairline treatment, etc., to prevent the ultraviolet rays in the disinfection channel from being reflected by the inner side wall of the shading channel 40 and leaking out. The shading channel 40 may also use, for example, a cloth curtain to enhance the shading effect.

In an exemplary embodiment of the disclosed technology, as shown in FIGS. 1 and 5, the shading channel 40 further includes a second connector 44 adapted to connect the top shading plate 41 to the frame 10. The second connector 44 includes a first connecting part adapted for connection (for example, bolted connection) with the top shading plate 41 and a second connecting part adapted for connection (for example, bolted connection) with the frame 10. The second connector 44 further includes a reinforcing part adapted for connection with the first connecting part and the second connecting part to enhance the robustness of the second connector 44.

In an exemplary embodiment of the disclosed technology, as shown in FIG. 1, the second connector 44 is made of a plate-shaped member by stamping.

In an exemplary embodiment of the disclosed technology, in order to further avoid leakage of the ultraviolet rays, it is preferable to provide a sealing strip at the connection between the shading channel 40 and the disinfection channel 20. In addition, sealing strips are also provided at connections between the base plate and the two side shading plates and at connections between the two side shading plates and the bottom shading plate of the disinfection channel. Similarly, sealing strips are also provided at connections between the top shading plate and the two side shading plates and at connections between the two side shading plates and the bottom shading plate of the shading channel.

In an exemplary embodiment of the disclosed technology, as shown in FIGS. 1 and 6, the conveyor 30 includes a driving roller 31 and a plurality of driven rollers 32. The driving roller 31 is driven, for example, by a driving device, to rotate, and the plurality of driven rollers 32 are driven by the driving roller 31, so as to realize the conveying of the tray. The driving roller 31 and the plurality of driven rollers 32 may be made of stainless steel, for example. However, those skilled in the art should understand that in some other embodiments of the disclosed technology, other forms of conveyors, such as conveyor belts, may also be used.

In this embodiment, the driving device for driving the driving roller 31 of the conveyor 30 may be connected, for example, to the controller 25, so as to control the operating state of the conveyor 30 through the controller 25.

In an exemplary embodiment of the disclosed technology, as shown in FIGS. 1 to 6, the frame 10 includes a frame body 11 and an adjustable foot 12 connected to the frame body 11. A level of the tray disinfection device may be adjusted by the adjustable foot 12 to ensure its stability.

The tray disinfection device for the security inspection system according to various embodiments of the disclosed technology rapidly kills bacteria and viruses on the surface of the tray by irradiating the tray during operation with the ultraviolet disinfection lamp arranged in the disinfection channel for a short time, thereby avoiding cross infection of related people caused by touching the tray, and protecting the health and safety of public places. The device may disinfect empty trays in transit in an intelligent passenger inspection system, and may also be used in civil aviation luggage check, postal parcel and mail sterilization and other occasions to disinfect luggage, parcel and mail.

Those skilled in the art may understand that the embodiments described above are exemplary and may be improved by those skilled in the art. The structures described in the various embodiments may be combined freely without conflicts in structure or principle.

Although the disclosed technology is described with reference to the drawings, the embodiments disclosed in the drawings are for illustrative purposes only and are not to be construed as limiting the disclosed technology.

Although some embodiments of the general concept of the disclosed technology have been illustrated and described, it should be understood by those ordinary skilled in the art that these embodiments may be changed without departing from the principle and the spirit of the general concept of the disclosed technology. The scope of the disclosed technology is defined by the appended claims and their equivalents.

It should be noted that the word "comprising" or "including" does not exclude other elements or steps, and the word "a", "an" or "one" does not exclude a plurality. In addition, any reference numerals in the claims should not be construed as limiting the scope of the disclosed technology.

What is claimed is:

1. A tray disinfection device for a security inspection system, comprising:
   a frame;
   a disinfection channel on the frame, wherein an ultraviolet disinfection lamp is arranged in the disinfection channel; and
   a conveyor on the frame, which is configured to convey a tray to pass through the disinfection channel, so as to disinfect the tray through an irradiation of the ultraviolet disinfection lamp,
   wherein the disinfection channel comprises:
   a base plate connected to the frame and located above the conveyor, wherein the ultraviolet disinfection lamp is installed on the base plate;
   a first bottom shading plate below the conveyor, and the first bottom shading plate is made of a mirror stainless steel; and
   two first side shading plates on both sides of the conveyor respectively,
   and wherein the two first side shading plates, the first bottom shading plate and the base plate enclose to form the disinfection channel;
   wherein at least one end of the conveyor along a conveying direction is provided with a shading channel in communication with the disinfection channel;
   wherein the shading channel comprises:
   a top shading plate connected to the frame and located above the conveyor;
   a second bottom shading plate below the conveyor; and
   two second side shading plates on both sides of the conveyor respectively;
   wherein the two second side shading plates, the second bottom shading plate and the top shading plate enclose to form the shading channel; and
   wherein inner surfaces of the top shading plate, the second bottom shading plate and the second side shading plates are subjected to blackening, frosting or hairline treatments.

2. The tray disinfection device according to claim 1, wherein at least part of an inner side wall of the disinfection channel is provided with a reflective layer.

3. The tray disinfection device according to claim 1, wherein a temperature control device is further arranged in the disinfection channel to control a temperature in the disinfection channel.

4. The tray disinfection device according to claim 1, wherein the disinfection channel further comprises a first connector adapted to connect the base plate to the frame.

5. The tray disinfection device according to claim 4, wherein the first connector is plate-shaped.

6. The tray disinfection device according to claim 1, wherein the shading channel further comprises a second connector adapted to connect the top shading plate to the frame.

7. The tray disinfection device according to claim 6, wherein the second connector is plate-shaped.

* * * * *